United States Patent
Park et al.

(10) Patent No.: US 8,164,123 B2
(45) Date of Patent: Apr. 24, 2012

(54) BIOSENSOR AND METHOD OF DRIVING THE SAME

(75) Inventors: Chan Woo Park, Daejeon (KR); Chang Geun Ahn, Daejeon (KR); Chil Seong Ah, Daejeon (KR); Tae Youb Kim, Seoul (KR); An Soon Kim, Daejeon (KR); Jong Heon Yang, Daejeon (KR); Gun Yong Sung, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 169 days.

(21) Appl. No.: 12/703,939

(22) Filed: Feb. 11, 2010

(65) Prior Publication Data

US 2011/0068015 A1   Mar. 24, 2011

(30) Foreign Application Priority Data

Sep. 22, 2009   (KR) .................. 10-2009-0089537

(51) Int. Cl.
*H01L 29/78* (2006.01)
*H01L 29/772* (2006.01)

(52) U.S. Cl. ........................... 257/253; 205/792
(58) Field of Classification Search .............. 204/435; 205/792; 257/253, E29.242
See application file for complete search history.

(56) References Cited

U.S. PATENT DOCUMENTS

| | | | |
|---|---|---|---|
| 4,020,830 A | 5/1977 | Johnson et al. | |
| 2002/0006632 A1 | 1/2002 | Ponnampalam et al. | |
| 2006/0121501 A1* | 6/2006 | Jabs et al. ................. | 435/6 |
| 2006/0205013 A1 | 9/2006 | Shim et al. | |
| 2006/0246478 A1* | 11/2006 | Yoo et al. ................. | 435/6 |
| 2007/0095664 A1 | 5/2007 | Chou et al. | |
| 2010/0072976 A1* | 3/2010 | Sheu et al. ............... | 324/71.1 |

FOREIGN PATENT DOCUMENTS

JP   2003-322633 A   11/2003
(Continued)

OTHER PUBLICATIONS

Toshiya Sakata, et al. "DNA Sequencing Based on Intrinsic Molecular Charges", Angewandte Chemie International Edition, vol. 45, Issue 14, pp. 2225-2228; Published Online: Feb. 28, 2006.

(Continued)

*Primary Examiner* — J. Christopher Ball
(74) *Attorney, Agent, or Firm* — Ladas & Parry LLP

(57) ABSTRACT

Provided are a biosensor and a method of driving the same. The biosensor includes a transistor including a substrate including a source, a drain, and a channel formed between the source and the drain, a gate insulating layer formed on the channel, and a source electrode and a drain electrode respectively connected with the source and the drain, a fluid line for covering the transistor to have an inner space together with the transistor and in which a sample solution including target molecules flows, a reference electrode formed on an inner wall of the fluid line, and a probe molecule layer attached on the reference electrode and reacting with the target molecules. Accordingly, the reference electrode is formed on the inner wall of the fluid line, enabling miniaturization of the bio device. Also, the probe molecules are formed on the reference electrode to measure a change in threshold voltage according to a change in electric potential between the reference electrode and the gate insulating layer, such that the sensitivity and reaction rate can be remarkably improved.

13 Claims, 2 Drawing Sheets

FOREIGN PATENT DOCUMENTS

| | | | |
|---|---|---|---|
| KR | 1020070054021 A | 5/2007 | |
| KR | 1020080050958 A | 6/2008 | |
| KR | 1020090058883 A | 6/2009 | |

OTHER PUBLICATIONS

Dong-Sun Kim, et al; "An extended gate FET-based biosensor integrated with a Si microfluidic channel for detection of protein complexes", Sensors and Actuators B, vol. 117, Issue 2, Oct. 2006 (exact date not given), pp. 488-494.

Ansoon Kim, et al; "Ultrasensitive, label-free, and real-time immunodetection using silicon field-effect transistors", Applied Physics Letters, 91, Published Sep. 4, 2007, pp. 103901-1 to 103901-3.

* cited by examiner

BIOSENSOR AND METHOD OF DRIVING THE SAME

CROSS-REFERENCE TO RELATED APPLICATION

This application claims priority to and the benefit of Korean Patent Application No. 10-2009-0089537, filed Sep. 22, 2009, the disclosure of which is incorporated herein by reference in its entirety.

BACKGROUND

1. Field of the Invention

The present invention relates to a biosensor and a method of driving the same, and more particularly to a biosensor in which a reference electrode and a fluid line are implemented in one body to enable miniaturization and a method of driving the same.

2. Discussion of Related Art

Among biosensors detecting biomolecules using an electrical signal, a transistor-based biosensor including a transistor has high electrical signal conversion speed and can be manufactured as an integrated circuit (IC). Thus, research on the transistor-based biosensor is actively under way.

FIG. 1 illustrates a conventional biosensor measuring a biological reaction using a field effect transistor (FET).

Referring to FIG. 1, in the conventional FET-based biosensor, a source and a drain 110 are formed on a substrate 100, and a channel 115 is formed between the source and drain 110.

A gate insulating layer 120 is formed on the channel 115, and a probe molecule layer 160 is formed on the gate insulating layer 120.

Meanwhile, source and drain electrodes 140 connected with the source and drain 110 are formed on an insulating layer 130, and an isolation layer 150 is formed on the source and drain electrodes 140.

As described above, the probe molecule layer 160 on the gate insulating layer 120 is exposed to the outside, and a sample solution 180 flows on the probe molecule layer 160.

Here, a reference electrode 190 for applying a gate voltage $V_{Gate}$ of a FET is dipped in the sample solution 180, and the gate voltage $V_{Gate}$ is transferred to the sample solution 180 by the reference electrode 190. A difference in electric potential between the reference electrode 190 and the sample solution 180 is kept uniform.

When target molecules 170 in the sample solution 180 are combined with probe molecules of the probe molecule layer 160 on the gate insulating layer 120, the electric potential of the surface of the gate insulating layer 120 is changed by electric charges that the target molecules 170 have. Thus, the value of a threshold voltage for applying current to the channel 115 under the gate insulating layer 120 is changed.

By reading the change in the threshold voltage of the FET, it is detected whether or not a reaction occurs. At this time, the reliability of the threshold voltage deteriorates unless the difference in electric potential between the reference electrode 190 and the sample solution 180 is kept uniform.

Also, since the reference electrode 190 must be dipped in the sample solution 180, it is difficult to reduce the size of the biosensor even if the FET is miniaturized. Consequently, there is a limit in increasing the sensitivity of the biosensor and reducing the measurement time.

SUMMARY OF THE INVENTION

The present invention is directed to a biosensor in which the structure of a reference electrode is changed to enable miniaturization.

One aspect of the present invention provides a biosensor including: a transistor including a substrate including a source, a drain, and a channel formed between the source and the drain, a gate insulating layer formed on the channel, and a source electrode and a drain electrode respectively connected with the source and the drain; a fluid line for covering the transistor to have an inner space together with the transistor, and in which a sample solution including target molecules flows; a reference electrode formed on an inner wall of the fluid line; and a probe molecule layer attached on the reference electrode and reacting with the target molecules.

A threshold voltage of the transistor may be changed according to a reaction between the probe molecules and the target molecules.

The reference electrode may receive a gate voltage applied from the outside to the sample solution.

The transistor may further include an insulating layer on the source electrode and the drain electrode.

The fluid line may be manufactured on a micrometer scale.

The substrate may be a silicon substrate.

The fluid line may be formed to cover the channel of the substrate.

The source electrode and the drain electrode may be disposed on the both sides of the fluid line.

Another aspect of the present invention provides a method of driving a biosensor including: attaching a probe molecule layer on a reference electrode of an inner wall of a fluid line; mounting the fluid line on a transistor whose gate insulating layer is exposed; flowing a fluid having no target molecules and measuring a threshold voltage of the transistor; and flowing a sample fluid having the target molecules and measuring a threshold voltage of the transistor.

The attaching of the probe molecule layer may be performed after the fluid line is mounted on the transistor.

The transistor and the fluid line may be manufactured on a micrometer scale.

A change in the threshold voltage of the transistor according to a reaction between the probe molecules of the biosensor and the target molecules may be measured.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Hereinafter, exemplary embodiments of the present invention will be described in detail. However, the present invention is not limited to the embodiments disclosed below but can be implemented in various forms. The following embodiments are described in order to enable those of ordinary skill in the art to embody and practice the present invention. Like numerals refer to like elements throughout the description of the drawings.

Throughout this specification, when an element is referred to as being "connected" or "coupled" to another element, it can be directly connected or coupled to the other element or intervening elements may be present.

Throughout this specification, when an element is referred to as "comprises," "includes," or "has" a component, it does not preclude another component but may further include the other component unless the context clearly indicates otherwise.

A biosensor according to an exemplary embodiment will be described below with reference to FIGS. 2 and 3.

Figure 1:
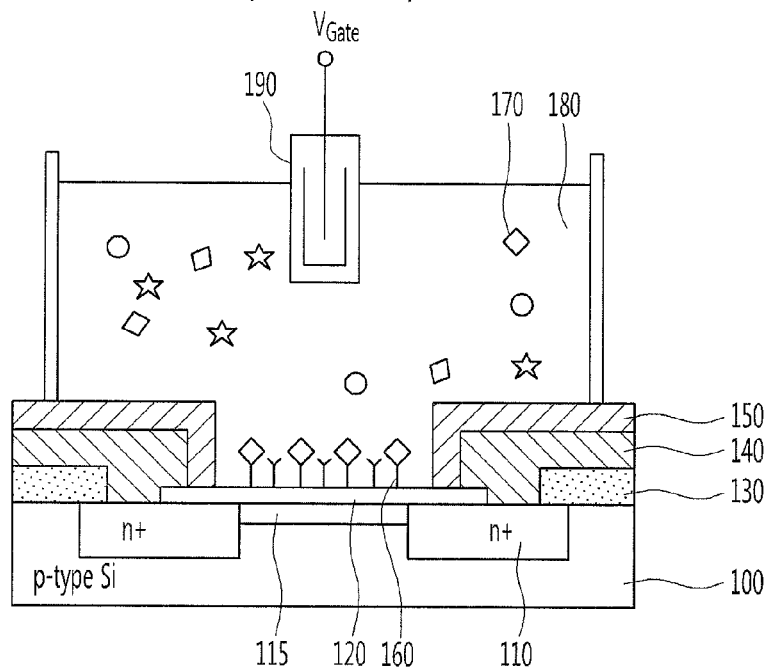
FIG. 1 illustrates a conventional biosensor measuring a biological reaction using a field effect transistor (FET)
Figure 2:
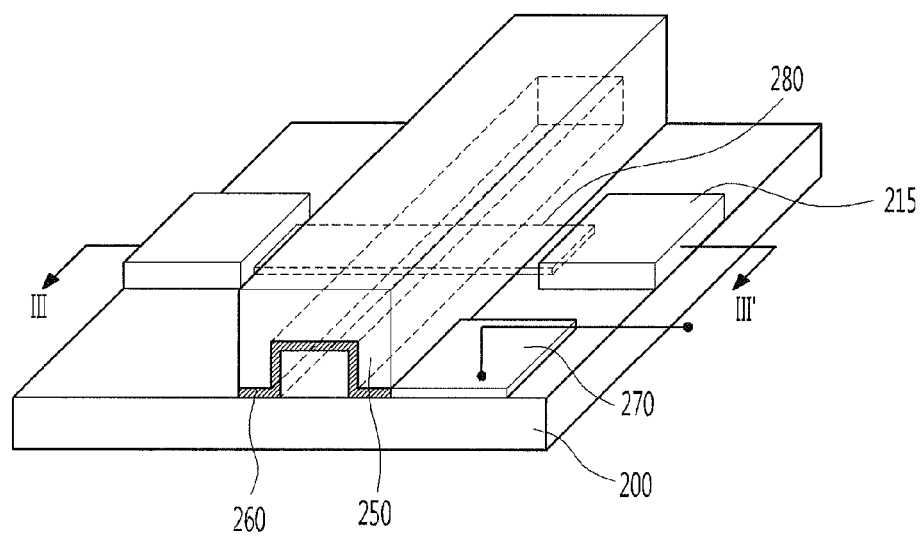
FIG. 2 illustrates a biosensor according to an exemplary embodiment of the present invention.
Figure 3:
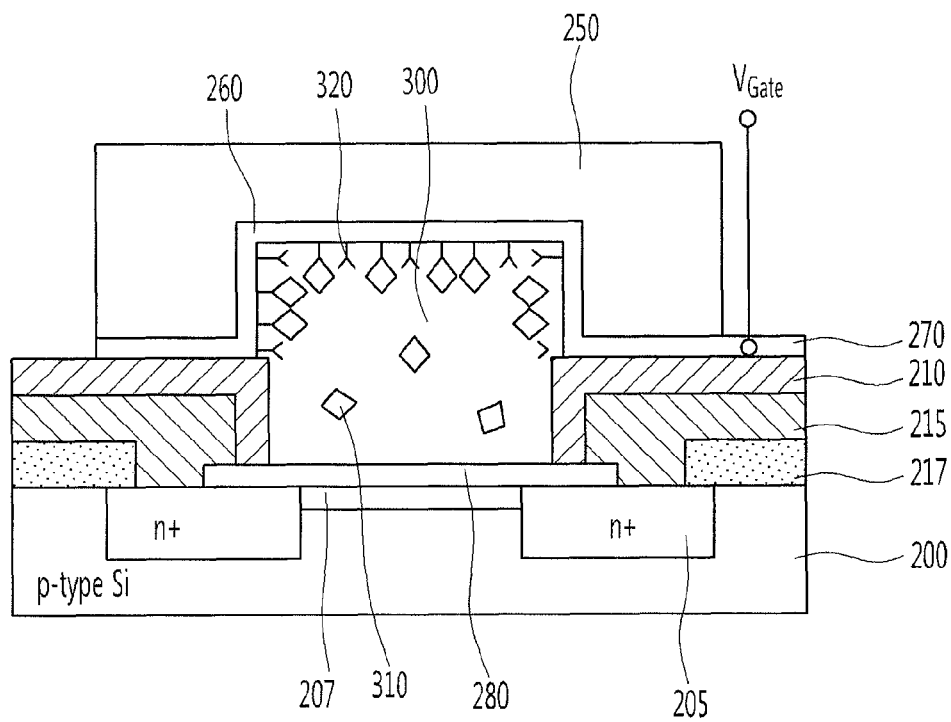
FIG. 3 is a cross-sectional view of the biosensor of FIG. 2.

FIG. 2 illustrates a biosensor according to an exemplary embodiment of the present invention, and FIG. 3 is a cross-sectional view of the biosensor of FIG. 2.

Referring to FIGS. 2 and 3, the biosensor according to an exemplary embodiment of the present invention includes a substrate 200 on which a field effect transistor (FET) is formed, and a fluid line 250.

The substrate 200 may be a p-type or n-type silicon substrate. In the case of a p-type silicon substrate, n-type impurities are doped in the substrate 200, thereby forming source and drain regions 205.

A channel 207 of the transistor is formed between the source and drain regions 205, and a gate insulating layer 280 is formed on the channel 207.

Meanwhile, an insulating layer 217 is formed in a part excluding the source and drain regions 205, and source and drain electrodes 215 connected with the source and drain regions 205 are formed on the insulating layer 217.

Here, the source and drain electrodes 215 may be a metal having a general conductivity.

On the source and drain electrodes 215, an isolation layer 210 is formed to cover the source and drain electrodes 215.

The transistor on the substrate 200 includes the channel 207 having a long width between the source and drain electrodes 215, and a gate pad 270 for applying a gate voltage $V_{Gate}$ is formed on one side of the transistor.

Meanwhile, the fluid line 250 has a long length to cross the channel 207 between the source and drain electrodes 215 on the substrate 200.

The fluid line 250 is formed to cover the gate insulating layer 280 of the transistor, and includes a space in which a sample solution 300 can flow.

On an inner wall of the fluid line 250, a reference electrode 260 is formed and stacked, and the reference electrode 260 is connected with the gate pad 270, which is formed on the substrate 200 to extend out of the fluid line 250, and receives the gate voltage $V_{Gate}$ from the outside.

Meanwhile, in the biosensor according to an exemplary embodiment of the present invention, a probe molecule layer 320 is formed on the reference electrode 260 disposed on the inner wall of the fluid line 250.

When target molecules 310 in the sample solution 300 are combined with the probe molecule layer 320 on the surface of the reference electrode 260, a difference in electric potential between the reference electrode 260 and the sample solution 300 is changed by electric charges of the target molecules 310. Thus, even if the uniform gate voltage $V_{Gate}$ is applied, the gate voltage $V_{Gate}$ actually applied to the channel 207 is changed.

As a result, an externally measured threshold voltage value of the FET is changed in proportion to the amount of the target molecules 310 combined with the probe molecule layer 320.

The FET is formed on the substrate 200, the fluid line 250 in which the reference electrode 260 is formed is mounted on the FET, and then the threshold voltage is measured by flowing the sample solution 300 through the inner space of the fluid line 250, so that the biosensor detects whether or not a reaction occurs.

Here, the probe molecule layer 320 may be attached to the reference electrode 260 before or after the fluid line 250 is mounted on the FET.

In this way, by forming the reference electrode 260 on the inner wall of the fluid line 250, the fluid line 250 can be manufactured on a micrometer scale according to the micrometer scale of the transistor, so that the bio device can be miniaturized.

Figure 4:
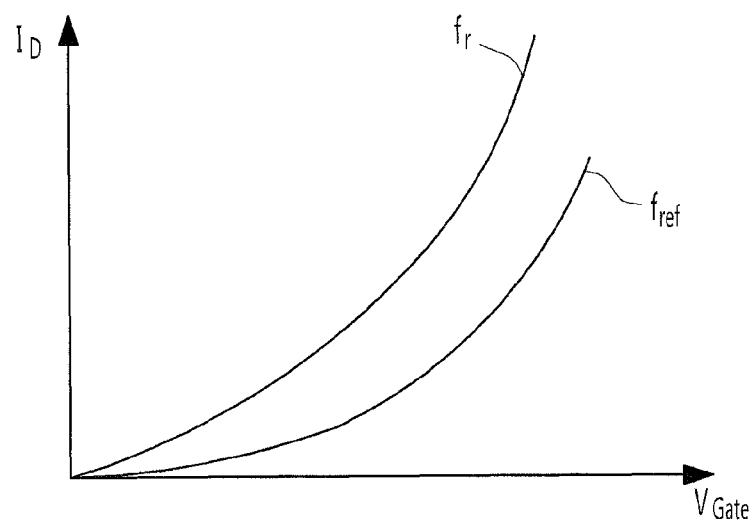
FIG. 4 shows characteristic curves of a biosensor according to an exemplary embodiment of the present invention.

FIG. 4 shows characteristic curves of a biosensor according to an exemplary embodiment of the present invention.

A reference characteristic curve $f_{ref}$ of a transistor with a probe molecule layer attached is different from a reaction characteristic curve $f_r$ after the probe molecule layer reacts with target molecules. In particular, a threshold voltage difference occurs.

In other words, the reaction characteristic curve $f_r$ according to a reaction between the target molecules and probe molecules shows that a threshold voltage moves with respect to the reference characteristic curve $f_{ref}$ of the transistor when a sample solution having no target molecules is flowed. The direction of the change in threshold voltage is determined according to whether the substrate is n type or p type.

It is possible to detect whether or not a reaction occurs based on the change in threshold voltage. Also, the volume of the fluid line is reduced to a micrometer scale, and thus a probability that respective target molecules in a sample solution are combined with a probe molecule layer increases when the same amount of the sample solution is supplied. Consequently, it is possible to remarkably improve the sensitivity and reaction rate of the sensor.

By forming a reference electrode on the inner wall of a fluid line according to an exemplary embodiment of the present invention, a bio device can be miniaturized. Also, since probe molecules are formed on the reference electrode to measure a change in threshold voltage according to a change in electric potential between the reference electrode and a gate insulating layer, the sensitivity and reaction rate can be remarkably improved.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A biosensor, comprising:
    a transistor including a substrate including a source, a drain, and a channel formed between the source and the drain, a gate insulating layer formed on the channel, and a source electrode and a drain electrode respectively connected with the source and the drain;
    a fluid line configured to cover the transistor to have an inner space together with the transistor, and in which a sample solution including target molecules flows;
    a reference electrode stacked on an inner wall of the fluid line, wherein the reference electrode is between the fluid line and the inner space; and
    a probe molecule layer attached on the reference electrode and configured to react with the target molecules.

2. The biosensor of claim 1, wherein a threshold voltage of the transistor is changed according to a reaction between the probe molecules and the target molecules.

3. The biosensor of claim 1, wherein the reference electrode receives a gate voltage applied from the outside to the sample solution.

4. The biosensor of claim 1, wherein the transistor further includes an insulating layer formed on the source electrode and the drain electrode.

5. The biosensor of claim 1, wherein the fluid line is manufactured on a micrometer scale.

6. The biosensor of claim 1, wherein the substrate includes a silicon substrate.

7. The biosensor of claim 5, wherein the fluid line is formed to cover the channel of the substrate.

8. The biosensor of claim 1, wherein the source electrode and the drain electrode are disposed on both sides of the fluid line.

9. A method of driving a biosensor, comprising:
   attaching a probe molecule layer to a reference electrode that is stacked on an inner wall of a fluid line;
   mounting the fluid line on a transistor whose gate insulating layer is exposed;
   flowing a fluid having no target molecules and measuring a threshold voltage of the transistor, and
   flowing a sample fluid having the target molecules and measuring a threshold voltage of the transistor.

10. The method of claim 9, wherein the attaching of the probe molecule layer is performed after the fluid line is mounted on the transistor.

11. The method of claim 9, wherein the transistor and the fluid line are manufactured on a micrometer scale.

12. The method of claim 9, wherein a change in the threshold voltage of the transistor according to a reaction between the probe molecules of the biosensor and the target molecules is measured.

13. The biosensor of claim 1 wherein the reference electrode does not go through the fluid line.

* * * * *